(12) United States Patent  
Singhatat

(10) Patent No.: US 7,713,286 B2
(45) Date of Patent: May 11, 2010

(54) KNOTLESS SUTURE ANCHOR

(75) Inventor: Wamis Singhatat, Santa Ana, CA (US)

(73) Assignee: Linvatec Corporation, Largo, FL (US)

( * ) Notice: Subject to any disclaimer, the term of this patent is extended or adjusted under 35 U.S.C. 154(b) by 1085 days.

(21) Appl. No.: 10/712,285

(22) Filed: Nov. 13, 2003

(65) Prior Publication Data
US 2004/0133239 A1 Jul. 8, 2004

Related U.S. Application Data

(60) Provisional application No. 60/426,553, filed on Nov. 15, 2002.

(51) Int. Cl.
*A61B 17/04* (2006.01)
*A61B 17/84* (2006.01)
*A61F 2/08* (2006.01)

(52) U.S. Cl. .................................. 606/232; 606/300

(58) Field of Classification Search ............... 606/220, 606/226–225, 228, 232, 72, 103, 224, 300; 24/115 R, 129 W, 130, 132 R, 133, 134 R, 24/134 L
See application file for complete search history.

(56) References Cited

U.S. PATENT DOCUMENTS

| | | | | |
|---|---|---|---|---|
| 5,236,431 A * | 8/1993 | Gogolewski et al. | .......... | 606/72 |
| 5,258,016 A * | 11/1993 | DiPoto et al. | ................ | 606/232 |
| 6,287,324 B1 * | 9/2001 | Yarnitsky et al. | ............. | 606/232 |
| 6,293,961 B2 * | 9/2001 | Schwartz et al. | ............. | 606/232 |
| 2003/0088272 A1 * | 5/2003 | Smith | ......................... | 606/232 |

* cited by examiner

*Primary Examiner*—(Jackie) Tan-Uyen T Ho
*Assistant Examiner*—Dianne Dornbusch
(74) *Attorney, Agent, or Firm*—Gene Warzecha

(57) ABSTRACT

The present invention provides a suture anchor capable of securing a suture to a body tissue.

14 Claims, 3 Drawing Sheets

KNOTLESS SUTURE ANCHOR

CROSS-REFERENCE TO RELATED APPLICATIONS

This application claims the benefit of U.S. Provisional Application No. 60/426,553, filed Nov. 15, 2002.

BACKGROUND

The present invention relates to surgical implants. In particular, the invention relates to suture anchors used to anchor a suture to a first portion of a body, the suture being used to attach a second portion of the body adjacent to the first portion. Still more particularly, the invention relates to a method and a suture anchor capable of securing a suture to a portion of a body without the need to tie any knots in the suture.

Suture anchors are often used in surgical procedures requiring the attachment of one tissue to another such as in attaching a soft tissue to a bone. Typical suture anchors are threaded or pressed into a hole drilled in the bone and include a suture that trails away from the anchor. The suture is then threaded through the tissue to be attached and knots are tied in the suture to hold the tissue against the bone adjacent the hole. One shortcoming of prior art suture anchors is the necessity of tying a knot which adds steps to the procedure, weakens the suture, and increases the complexity of the operation, especially in the tight confines of an arthroscopic or minimally invasive surgical wound.

SUMMARY

The present invention provides a suture anchor capable of securing a suture to a body tissue.

In one aspect of the invention, a suture anchor includes a distal body portion for securing the suture anchor in body tissue, an aperture for receiving a portion of the suture, and a deformable body portion for deforming the aperture to compress and grip the suture.

In another aspect of the invention, a unitary suture anchor includes a distal body portion for securing the suture anchor to a bone. A proximal body portion secures the suture to the suture anchor and includes a pair of elongated and relatively movable first body members. At least one of the first body members is hingedly connected to the distal body portion and the first body members are relatively movable between a suture receiving position and a suture locking position. A transverse suture receiving aperture is interposed between the first body members for receiving the suture when the first body members are in the suture receiving position. The aperture is deformed to grip the suture when the first body members are in the suture locking position.

In another aspect of the invention, a method for securing a suture to a body tissue, includes: providing a suture anchor having a distal body portion for securing the suture anchor in the body tissue, an aperture for receiving a portion of the suture, and a deformable body portion for deforming the aperture to compress and grip the suture; inserting a portion of the suture through the aperture; deforming the deformable body portion to deform the aperture and grip the suture; and inserting the suture anchor into the body tissue.

BRIEF DESCRIPTION OF THE DRAWINGS

Various examples of the present invention will be discussed with reference to the appended drawings. These drawings depict only illustrative examples of the invention and are not to be considered limiting of its scope.

DESCRIPTION OF THE ILLUSTRATED EMBODIMENTS

Figure 1:
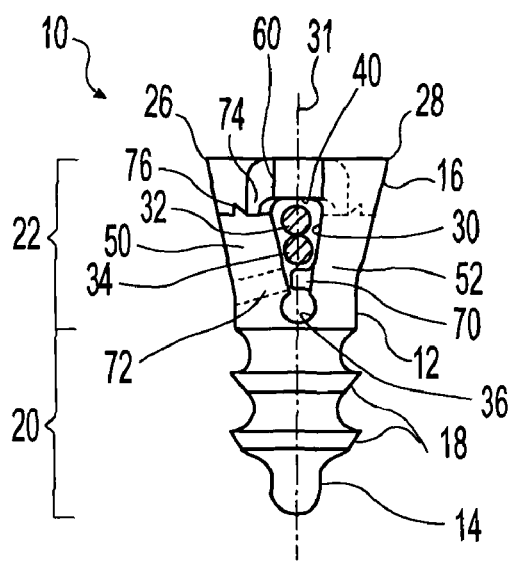
FIG. 1 is a front plan view of an illustrative suture anchor according to the present invention and shown in an open position.
Figure 2:
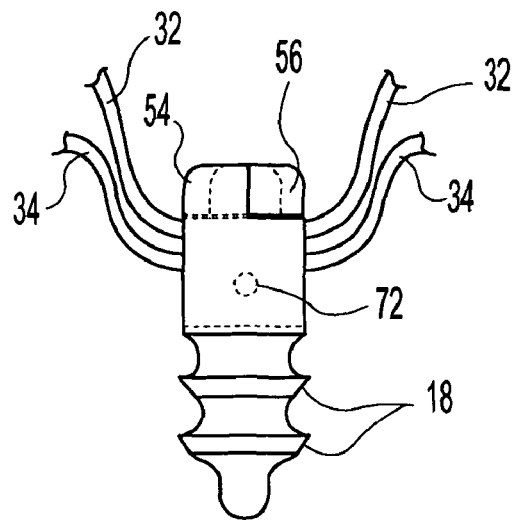
FIG. 2 is a side plan view of the suture anchor of FIG. 1.

Embodiments of a suture anchor include a portion for anchoring the suture anchor in tissue and a portion for gripping a suture. These portions may be separate components or may be combined into a single multipurpose component. The suture anchor of the present invention may be used to anchor a suture to any appropriate tissue. The anchor portion of the suture anchor may include a variety of configurations to adapt it for use in tissues having different mechanical properties. For example, the anchor may be adapted for use in meniscus, cartilage, cancellous bone, cortical bone and/or other soft and hard tissues. The anchor may be used to attach muscle tissue, cartilage, bone, prosthetic devices and/or other substances via the suture and suture gripping portion. For example, the suture anchor may be used to attach soft tissues associated with the skeletal system to a bone such as a ligament to the bone surrounding a skeletal joint. The joint may include the hip, knee, shoulder, wrist, elbow, ankle, vertebral, phalangeal, temporomandibular, and other joints and locations within a patient's body. In another example, the suture anchor may be used to attach a non-skeletal soft tissue to a bone such as attaching a urinary structure to the pelvic bone. In another example, the suture anchor may be used to attach a soft tissue or prosthetic device within a body cavity such as anchoring soft tissue or a prosthetic device to the abdominal wall. Other examples of attaching items together within a patient's body will be apparent and fall within the scope of the invention.

In the illustrative embodiments, a suture anchor is depicted for use in securing a portion of the rotator cuff to a bone adjacent a human shoulder joint. It will be understood by those skilled in the art that this application is illustrative only and that the suture anchor is usable in other applications.

FIGS. 1-5 show an illustrative knotless suture anchor 10 including a body 12 having a distal end 14 configured to be anchored in a bone and a proximal end 16 configured to grip a suture. In the illustrative suture anchor 10, the distal end 14 includes annular ribs 18 adapted to engage a predrilled hole in the bone. It will be understood that numerous other types of anchoring mechanisms, other than annular ribs, may be employed with the knotless suture anchor concepts embodied in the suture anchor 10 and that these concepts may be embodied in a suture anchor 10 requiring a predrilled hole or one that may be inserted without predrilling. For example, the anchoring mechanism may include hooks, barbs, screw threads, expanding members, wires, prongs, and/or other suitable mechanisms.

Figures 3, 4:
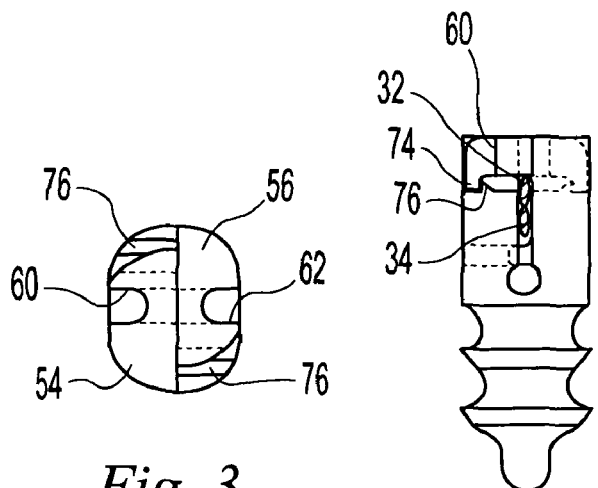
FIG. 3 is a top plan view of the suture anchor of FIG. 1.
FIG. 4 is a front plan view of the suture anchor of FIG. 1 shown in a closed position.
Figure 5:
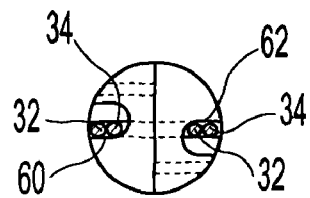
FIG. 5 is a top plan view of the suture anchor of FIG. 1 shown in a closed position.

The suture anchor 10 further includes a distal, generally cylindrical body portion 20 and a proximal body portion 22 having a distally tapering, variable cross-section. The juncture between the distal and proximal body portions 20, 22 is cylindrical and fixed in cross-section in order to provide a smooth transition between the body portions 20, 22. The proximal body portion 22 has an open position (FIGS. 1 and 3) and a closed position (FIGS. 4 and 5). As may be seen by comparing FIGS. 1-5, the proximal body portion 22 has a conical profile when viewed from the front in the open position (FIG. 1), a cylindrical profile when viewed from the side (FIG. 2), a generally oval profile when viewed from the top in the open position (FIG. 3), and a cylindrical profile when viewed from the front and top in the closed position (FIGS. 4 and 5).

The diameter of the distal body portion 20 is selected to be slightly greater than the diameter of the hole into which the anchor 10 is to be inserted. The diameter of the proximal body portion 22 in the closed position is designed to be similar to that of the distal body portion 20. However, the major diameter of the proximal body portion 22 when it is in the open position (FIG. 3) is greater than the diameter of distal body portion 20.

The open and closed positions are made possible by the formation of the proximal body portion 22 as two diametrically opposed gripping sections 26, 28 which are movable radially inwardly relative to each other. As shown in FIG. 1, the gripping sections 26, 28 are separated by an axially aligned tapered suture receiving aperture 30 which is adapted to receive at least two strands of suture 32, 34. The aperture 30 extends transversely entirely through the proximal body portion 22 and has a distal, transverse stress relieving aperture 36 and a top surface 40. The aperture 30 is aligned along the axis 31 of the suture anchor 10 and is sized to receive the suture strands 32, 34 in a vertical orientation as shown in FIG. 1.

The gripping sections 26, 28 have semi-cylindrical distal longitudinal body members 50, 52, respectively, and proximal ends made in the form of transverse body members 54, 56, respectively. Each transverse body member 54, 56 has a generally semi-circular profile when viewed from the top as shown in FIGS. 3 and 5. The transverse body members 54, 56 are integrally formed with their respective longitudinal body members 50, 52 and are arranged to slide relative to one another, as best seen by comparing FIGS. 3 and 5. The longitudinal body members 50, 52 are integrally formed with the distal body portion 20. The suture anchor 10 is made of a material that is sufficiently resilient to enable limited pivoting motion of the longitudinal body members 50 and 52 about their juncture with distal body portion 20, from the open position shown in FIGS. 1 and 3 radially inwardly to the closed position shown in FIGS. 4 and 5. When the suture anchor 10 is in the open position, the sutures can slip through the aperture 30 to permit their initial placement in the aperture 30 and subsequent tightening, as shown in FIG. 1. When the suture anchor 10 is in the closed position, it compresses the sutures 32, 34 and grips them so that they do not slip through the aperture 30, as shown in FIG. 4.

Each transverse body member 54, 56 is provided with a suture channel 60, 62 for receiving portions of the suture strands 32, 34. The channels 60, 62 are sized such that when the suture anchor 10 is closed, the suture strands 32, 34 may be recessed within the channels 60, 62 so that they are not abraded by the adjacent bone, as shown in FIG. 5.

The suture receiving aperture 30 further includes a projection 70 extending from one of the longitudinal body members 52 and spaced above the aperture's 30 distal end. This projection 70 is intended to prevent the sutures 32, 34 from entering the distal end of the aperture 30 where they might interfere with the movement of the gripping sections 26, 28. The projection 70 also prevents the sutures 32, 34 from entering the stress relieving aperture 36 where they might not be gripped as tightly as desired. A through hole 72 is formed in the other longitudinal body member 50 opposite the projection 70 to receive the projection 70. In the open position, the projection reaches to, or into, the through hole 72 so that the sutures 32, 34 cannot move around the projection. In the closed position, the projection 70 extends further into the through hole 72 so that the projection 70 does not interfere with the movement of the gripping sections 26, 28.

The illustrative suture anchor 10 of FIGS. 1-5 further includes an optional ratchet and pawl type locking mechanism to retain the suture anchor 10 in the closed position. Each transverse body member 54, 56 includes a pawl 74 projecting distally and each longitudinal body member 50, 52 includes a tooth 76 projecting proximally and engageable with the pawl 74. When the suture anchor 10 is moved into the closed position, the pawl 74 snaps over the tooth 76 and grips the tooth 76 to hold the suture anchor in the closed position.

Figures 6, 7, 8:
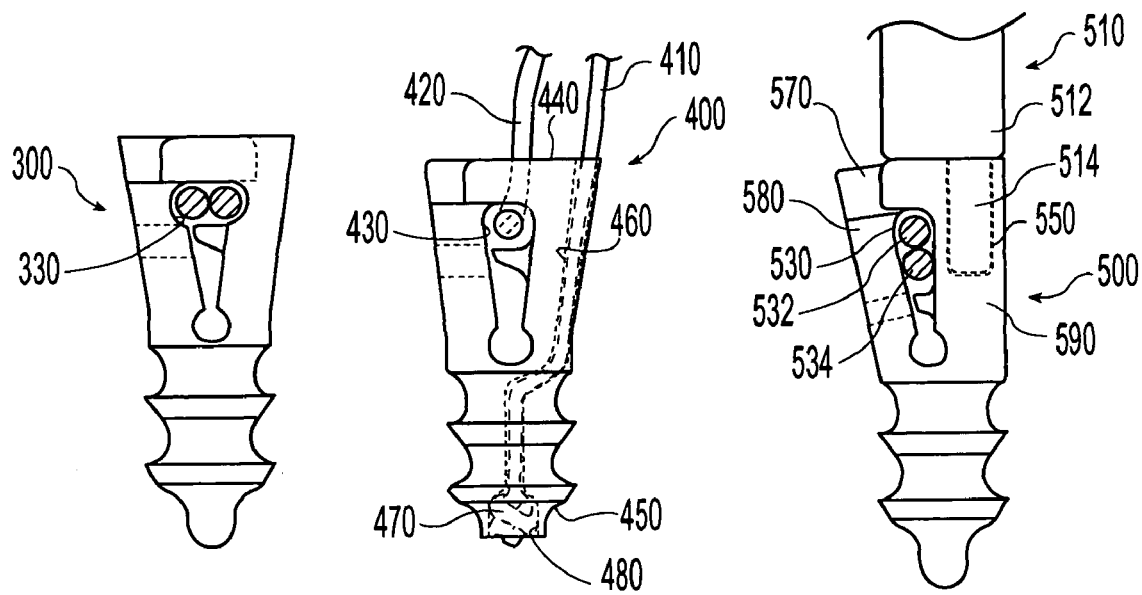
FIG. 6 is a front plan view of the suture anchor of FIG. 1 shown with an optional horizontal eyelet in the open position.
FIG. 7 is a front plan view of the suture anchor of FIG. 1 shown with an optional preloaded suture in the open position.
FIG. 8 is a front plan view of the suture anchor of FIG. 1 shown with an optional driver interface in the open position and assembled to a driver.

FIG. 6 depicts an alternative suture anchor 300 having a horizontal suture aperture 330 adapted to receive suture ends in a horizontal configuration.

FIG. 7 depicts an alternative suture anchor 400 in which a first end 410 of the suture is permanently attached to the suture anchor 400 body and a second end 420 of the suture is received by the suture receiving aperture 430. The first end 410 is threaded through a longitudinal opening 460 from the proximal end 440 of the suture anchor 400 to the distal end 450 of the suture anchor 400. A knot 470 is tied in the first end 410 to prevent it from pulling back through the opening 460. A recess 480 formed at the distal end 450 receives the knot 470 to protect it from abrasion and keep it out of the way during insertion of the suture anchor 400. The first end 410 may be attached to the suture anchor 400 in a variety of other ways including adhering, welding, fusing, crimping, insert molding and/or other suitable methods. In use, the second end 420 is threaded through the tissue to be secured and then through the aperture 430.

The various suture anchors described above may be inserted into proper position within a bone by being driven by a driver attached to the proximal end of the suture anchors. An illustrative driver 510 is shown in FIG. 8 attached to a suture anchor 500. The suture anchor 500 is further depicted in FIGS. 9 and 10. The driver 510 has an elongated, generally cylindrical shaft 512 with a projection 514 extending distally from the distal end of the shaft 512. The projection 514 is received by a recess 550. In the illustrative driver 510, the projection 514 and recess 550 have a non-circular cross-section to prevent the suture anchor 500 from rotating relative to the driver 510. The suture anchor 500 is constructed similarly to the above described suture anchors except that the suture receiving aperture 530 is offset laterally, rather than being axially aligned. The aperture 530 is offset laterally to provide room for the recess 550 formed in the top of the suture anchor 500 and extending distally into the suture anchor 500 to receive the projection 514. The proximally facing surface 562 of the transverse body member 560 abuts the end of the shaft 512 when the projection 514 is received in the recess 550 to enable transmission of sufficient distally directed axial force to seat the anchor 500 in a bone hole. The proximally facing surface 562 and transverse member 560 associated with the longitudinal body member 590 do not move laterally within the bone hole as the anchor 500 is being seated. However the transverse member 570 associated with longitudinal body member 580 deforms radially inwardly to compress the suture ends 532, 534. As with the other above described suture anchors, the radially inward deformation of the suture aperture 530 is caused by the relative motion between the body portions of the suture anchor.

Figures 9, 11:
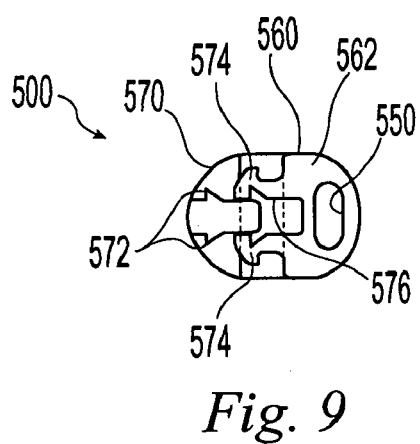
FIG. 9 is a top plan view of the suture anchor of FIG. 8 shown with an optional locking mechanism in the unlocked position.
FIG. 11 is a top plan view of the suture anchor of FIG. 8 shown with an optional locking mechanism in the unlocked position.
Figure 10:
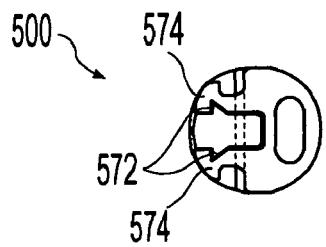
FIG. 10 is a top plan view of the suture anchor of FIG. 8 shown with the optional locking mechanism of FIG. 9 in the locked position.

As seen in FIGS. 9 and 10, an alternative ratchet and pawl mechanism is provided on the mating components of the top portions of the suture anchor 500 to aid in maintaining the suture aperture 530 in the closed position. The mechanism includes opposing teeth 572 and pawls 574 and operates similarly to the above described ratchet and pawl mechanisms. In the mechanism shown in FIGS. 9-10, two pawls 574 are mounted on one transverse member 560 and face one another to create a "U"-shaped opening 576. Two teeth 572 are mounted on the other transverse member 570 and face outwardly. When the suture anchor 500 is moved into the closed position, the teeth 572 press the pawls 574 radially outwardly until the tips of the pawls 574 move past the teeth 572 at which point the pawls 574 snap radially inwardly behind the teeth 572 to grip the teeth 572 and hold the suture anchor 500 in the closed position.

Figure 12:
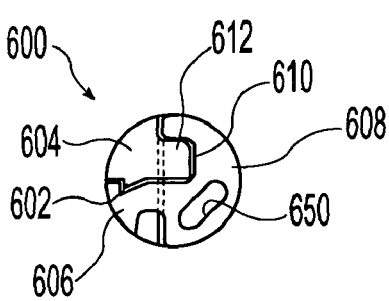
FIG. 12 is a top plan view of the suture anchor of FIG. 8 shown with the optional locking mechanism of FIG. 11 in the locked position.

FIGS. 11 and 12 depict a suture anchor 600 having an alternative asymmetrical locking mechanism and driver interface. The mechanism includes a tooth 602 mounted on one transverse member 604 along the centerline of the suture anchor 600 and a pawl 606 mounted on the other transverse member 608 opposite the tooth 602. The pawl 606 carrying transverse member 608 further includes a "U"-shaped recess 610 opposing a lug 612 projecting from the tooth 602 carrying transverse member 604. When the transverse members 604, 608 are moved to the closed position (FIG. 12), the pawl 606 snaps over the tooth 602 to hold the mechanism closed. The lug 612 is also received by the "U"-shaped recess 610 to keep the transverse members 604, 608 aligned and to provide side-to-side rigidity to the locking mechanism. A driver receiving recess 650 is formed off-center in the top of the pawl 606 carrying transverse members 608.

Figure 13:
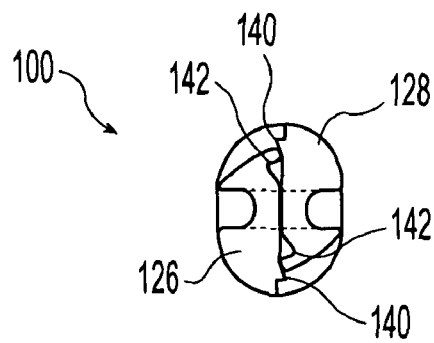
FIG. 13 is a top plan view of the suture anchor of FIG. 1 shown with an optional locking mechanism in the unlocked position.
Figure 14:
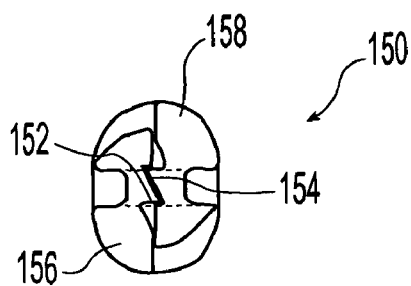
FIG. 14 is a top plan view of the suture anchor of FIG. 1 shown with an optional locking mechanism the unlocked position.

FIGS. 13 and 14 depict additional variations in the locking mechanism of FIGS. 1-5. In FIG. 13, a suture anchor 100 may include a distal body portion identical to suture anchor 10 and a proximal body portion having modified transverse body members in the form of transverse body members 126, 128 provided with a side-locking ratchet and pawl mechanism. Each transverse body member 126, 128 includes a projection 140 on one end and a recess 142 on the other end opposite the projection 140 on the other transverse body member. When the transverse body members 126, 128 are moved into the closed position, the projections 140 snap into the recesses 142 to retain the suture anchor 10 in the closed position. The suture anchor 10 shown in FIG. 13 has a ratchet and pawl mechanism positioned symmetrically on either side of the axis of suture anchor 100 at each end of the transverse body members 126, 128. The alternate suture anchor 150 of FIG. 14 has a similar mechanism with complimentary teeth 152, 154 on transverse body members 156, 158 formed near the center of the suture anchor 150.

The suture anchor 10 may be a unitary or multi-piece construction including any suitable biocompatible materials. Exemplary materials include metals, polymers, and/or other suitable materials and combinations thereof. For example, the suture anchor 10 may include metals including stainless steels, titanium, titanium alloys, tantalum, cobaltchromium steels, nickel-titanium alloys, and/or others. The suture anchor 10 may include nonresorbable polymers including polyolefins, polyesters, polyimides, polyamides, polyacrylates, poly(ketones), fluropolymers, siloxane based polymers, and/or others. The suture anchor 10 may include resorbable polymers including polyesters (e.g. lactide and glycolide), polyanhydrides, poly(aminoacid) polymers (e.g. tyrosine based polymers), and/or others. The suture anchor 10 may include other materials that provide sufficient flexibility for the longitudinal body members to flex relative to one another. The suture anchor 10 may further include osteoconductive and/or osteoinductive additives to facilitate and/or stimulate bone growth at the anchor 10 location. Exemplary additives include hydroxyapitite, beta tricalcium phosphate, bone growth proteins, and/or other suitable materials. The suture anchor may be constructed by machining, punching, welding, molding, sintering, and/or other suitable methods. For example, a suitable suture anchor 10 may be injection molded from a resorbable polymer such as polylactic acid polymer.

Figure 15:
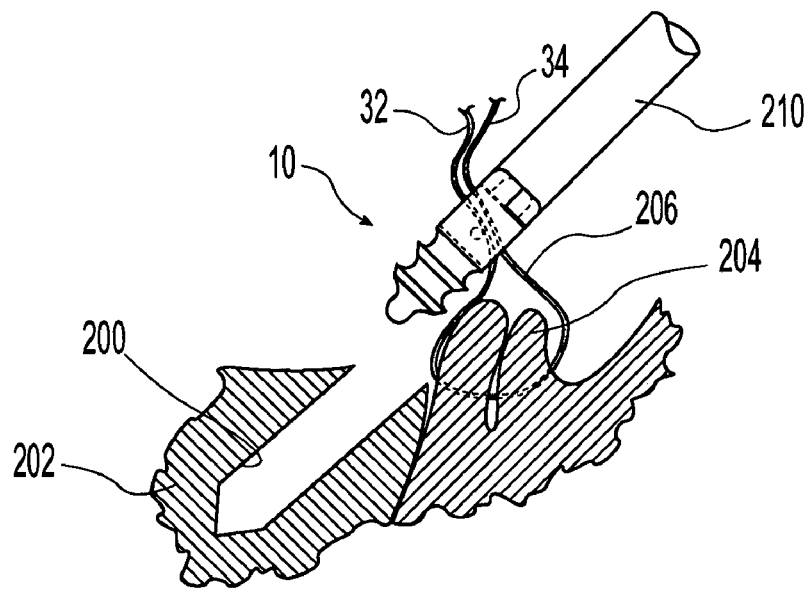
FIGS. 15-17 are partial side section views showing the stages of use of the suture anchor of FIG. 1.
Figure 16:
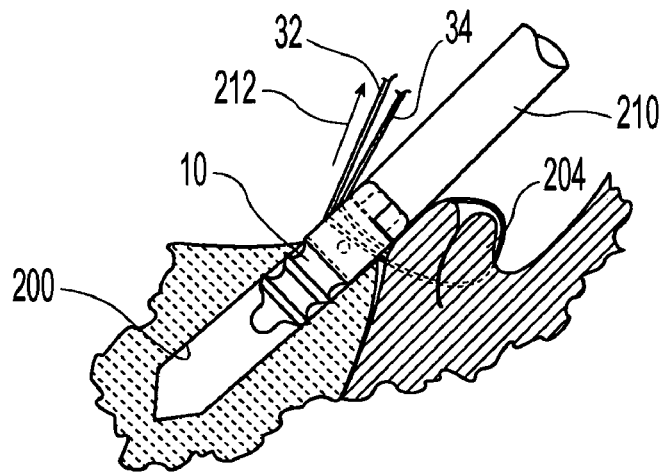
Figure 17:
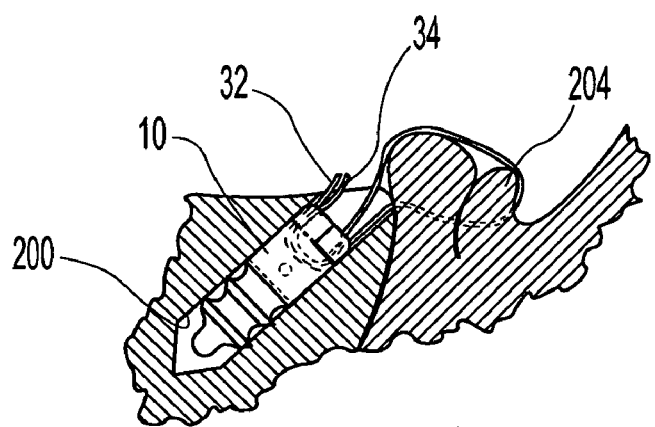

The use of the suture anchor 10 of FIGS. 1-5 is shown in FIGS. 15-17. A hole 200 is drilled in a bone 202 to which tissue 204 is to be attached. A suture 206 is passed through the tissue 204 in a conventional manner and the ends 32, 34 of the suture 206 are threaded through the aperture 30 of the suture anchor 10. The suture anchor 10 is situated at the distal end of a driver 210 and is pushed by the driver 210 into the hole 200 while proximally directed tension 212 is applied to the suture ends 32, 34. As the suture anchor 10 enters the hole 200, the proximal body portion 22 is compressed from a generally conical/oval configuration as shown in FIGS. 1 and 3 into a cylindrical configuration as shown in FIGS. 4 and 5 by the cylindrical wall of the hole 200. As the gripping sections 26, 28 are pressed inwardly, they compress and grip the suture ends 32, 34. Thus, as shown in FIG. 17, when the anchor 10 is seated properly in the hole 200, the suture ends 32, 34 will be crimped within the aperture 30 and thereby secure the tissue 204 without the necessity of forming a knot in the suture 206. Alternatively, the proximal body portion 22 may be compressed manually outside of the hole 200 prior to insertion of the suture anchor 10. This alternative may be advantageous for example where the suture anchor 10 is being inserted into relatively soft bone tissue or tissues other than bone. Once the suture anchor 10 is seated, the suture ends 32, 34 may be trimmed as shown in FIG. 17.

It will be understood by those skilled in the art that numerous improvements and modifications may be made to the preferred embodiment of the invention disclosed herein without departing from the spirit and scope thereof.

What is claimed is:

1. A suture anchor for insertion into a cylindrical bone hole to anchor a suture to bone, the suture anchor comprising:

a distal body portion defining a longitudinal axis, the distal body portion having a diameter sufficient to fit in said bone hole, being insertable into the bone holes and defining a radially outwardly projecting anchoring member operable to retain the suture anchor in the bone hole; and a proximal body portion integrally formed with and extending longitudinally from the distal body portion, the proximal body portion having opposed gripping portions moveable transversely between an open position and a closed position, the gripping portions defining a transverse, suture receiving aperture between them for receiving a transversely oriented section of at least one suture, wherein the aperture is relatively larger and able to receive the suture, in two-way, free sliding relationship when the gripping portions are in the open position, wherein the aperture is relatively smaller and able to grip the suture in gripping relationship so the suture is prevented from moving in any direction when the gripping portions are in the closed position, wherein the proximal body portion is responsive to insertion into the bone hole to move the gripping portions from the open to the closed position as the suture anchor is pushed into the bone hole, wherein the proximal body portion has a maximum transverse dimension in the open position, the proximal body portion has a smaller maximum transverse position in the closed position, and the anchoring member has a maximum transverse dimension smaller than the maximum transverse dimension of the proximal body portion in the open position, wherein the gripping portions form a top surface portion of the transverse aperture that encloses a portion of the transverse aperture in the proximal direction, and wherein the gripping portions extend over and beyond the transverse aperture while the suture anchor is in the open position so the transversely oriented section of each suture is prevented from exiting the aperture longitudinally.

2. The suture anchor of claim 1 wherein the proximal body portion includes at least one channel extending proximally from the aperture to receive the suture in a recessed protected position.

3. The suture anchor of claim 2, wherein each channel extends from the transverse aperture and opens through the proximal body portion.

4. The suture anchor of claim 1 wherein the anchoring member comprises at least one annular ring transverse to the longitudinal axis of the distal body portion.

5. The suture anchor of claim 1, wherein the proximal body portion further comprises a locking mechanism operable to retain the proximal body portion in the closed position.

6. The suture anchor of claim 5 wherein the locking mechanism comprises a first portion defining a lock projection and a second portion defining a lock recess for receiving the lock projection, the first and second portions sliding adjacent one another between the open and closed positions, the lock projection positively engaging the lock recess in the closed position.

7. The suture anchor of claim 1 wherein the aperture is elongated longitudinally to receive at least two suture ends extending transversely and spaced longitudinally within the aperture.

8. The suture anchor of claim 1 wherein the aperture is elongated transversely to receive at least two suture ends extending transversely and spaced transversely in a direction orthogonal to the axis of the suture within the aperture.

9. The suture of claim 1 further comprising a suture wherein the suture has first and second ends, the first end being fixed to the suture anchor and the second end being receivable by the aperture in the open position to form a sliding suture loop, the second end being gripped by the aperture in the closed position to form a fixed suture loop.

10. The suture anchor of claim 1, further comprising at least one channel defined by a void in the portion of one gripping portion extending over and beyond the transverse aperture.

11. A unitary suture anchor for securing a suture into a cylindrical bone tunnel without tying a knot comprising:

a distal body portion comprising an anchor member operable to secure the suture anchor to the bone;

a proximal body portion comprising a pair of elongated and relatively movable first body members, at least one of the first body members being hingedly connected to the distal body portion, the first body members being relatively movable between a suture receiving open position and a suture locking closed position, said proximal body portion having a generally elliptical cross-sectional shape when said elongated first body members are in the suture receiving position and a generally circular cross-sectional shape when said elongated first body members are in the suture locking position within the bone tunnel;

a transverse suture receiving aperture interposed between the first body members, the aperture adapted to receive a transversely oriented section of at least one suture in two-way, free sliding relationship when the first body members are in the suture receiving open position, the aperture being deformed and gripping the suture when the first body members are in the suture locking closed position; and a locking mechanism comprising a transverse body member extending from each of the first body members, the transverse body members being in sliding contact from the open position to the closed position, the transverse body members defining a male/female engagement mechanism in which a portion of one transverse body member snaps over a portion of the other transverse body member in positive engagement to lock the first body members in the suture locking position, wherein a top surface portion of the transverse aperture enclosing a portion of the transverse aperture in the proximal direction is at least one gripping portion extending over and beyond the transverse aperture while the suture anchor is in the open position so the transversely oriented section of each suture is prevented from exiting the aperture longitudinally.

12. The suture anchor of claim 11 wherein the suture anchor comprises a bioabsorbable material.

13. The suture anchor of claim 11 wherein the proximal body portion includes at least one channel extending proximally from the aperture to receive the suture in a recessed protected position.

14. The suture anchor of claim 13, wherein each channel extends from the aperture and opens through one of the transverse body members.

* * * * *